//  
United States Patent [19]
Anderson

[11] 4,035,719
[45] July 12, 1977

[54] CONDUCTIVITY CELL

[75] Inventor: Robert L. Anderson, Boulder, Colo.

[73] Assignee: Halbert Fischel, Encino, Calif.

[21] Appl. No.: 599,691

[22] Filed: July 28, 1975

[51] Int. Cl.² ..................................... G01N 27/42
[52] U.S. Cl. .......................... 324/30 R; 324/30 B
[58] Field of Search ................ 324/29, 30 R, 30 B, 324/65 R; 204/195 R

[56] References Cited

U.S. PATENT DOCUMENTS

| | | | |
|---|---|---|---|
| 2,774,732 | 12/1956 | Blight | 324/30 B |
| 2,834,937 | 5/1958 | Raynor | 324/30 B |
| 2,950,176 | 8/1960 | Thager et al. | 324/30 B |
| 3,242,729 | 3/1966 | Keller | 324/30 B |
| 3,936,738 | 2/1976 | Maltby | 324/30 R |

Primary Examiner—Rudolph V. Rolinec
Assistant Examiner—Michael J. Tokar
Attorney, Agent, or Firm—Fraser and Bogucki

[57] ABSTRACT

The conductivity of an electrolytic solution is determined with accuracy and sensitivity by measuring the conductance along extended paths of small cross-sectional areas between large area electrodes. Current flow is thereby measured with minimization of distortion effects created by electrolytic depositions or other form of electrode surface contamination. Further, sensitivity and reliability are enhanced by employing conductivity cell sections as variable resistance arms in a bridge excited with an extremely low voltage, low duty cycle AC signal which is filtered and synchronously demodulated to provide the desired conductivity measurement.

18 Claims, 7 Drawing Figures

CONDUCTIVITY CELL

BACKGROUND OF THE INVENTION

Conductivity cells must often operate to determine precise quantities of an electrolyte in a solution such as salts in a biological solution or a dialysate used in a kidney machine. It is often necessary to maintain conductivity within predetermined limits. Prior art conductivity cells and the electrical systems associated therewith generally pass a current through the electrolytic solution, measuring the voltage differential between a pair of electrodes. Such systems typically employ a spaced-apart pair of electrodes of limited area and have an accuracy substantially no greater than several percent after compensation. This accuracy is a fundamental limitation of the prior art systems which cannot be improved with special circuitry or other adaptations regardless of cost. Limitations on accuracy are encountered because the electrolytic solution induces battery and plating effects, because the conductivity cell is sensitive to electrode surface contamination and because cell measurements are sensitive to stray fields. The geometries of the cell and of the electrodes have a significant effect on cell stability because there is a relationship between surface and fluid resistance which results therefrom. Probe surface resistance, boundary layer resistance and electrical noise in the fluid, as well as variables in the signal processing system have adverse effects on stability and sensitivity.

SUMMARY OF THE INVENTION

In conductivity cells for concentration control systems in accordance with the invention, the conductivity of a fluid is measured by passing a known current along elongated, smooth-walled dielectric fluid paths of small cross-sectional area between substantially larger volume electrode chambers. The geometry of the fluid passageway-electrode system provides small cross-sectional area and long signal conductance sections of high impendance, together with high aspect ratio electrode surfaces of low surface impedance and minimizes the effects of surface contamination, charge buildup, and variations in probe surface resistance.

In a more particular example of a system in accordance with the invention, the conductivity cell of defined geometry is disposed in a circuit configuration that takes superior advantage of the cell properties to provide a conductivity control loop which is consistently within ± 0.1% of said value and maintains transient variations at less than 1%. The conductivity cell is utilized as one arm of a balanced bridge which includes a temperature compensating thermistor that is responsive to the fluid temperature. A mix ratio error signal is proportional to input balance current required to balance the bridge. Reading of the conductance is in a stable, timed cycle in which the total duty cycle interval has a greater than 10:1 relation to an active read signal portion thereof. The cell is coupled in a bridge and AC excited with a low amplitude signal at a selected frequency. A low level bridge balancing output signal is preamplified, filtered and then synchronously demodulated to provide periodic pulses of amplitude corresponding to the conductivity reading. A read and hold cirucit converts the pulses to a steady state control signal which controls a servo motor drive for a mix ratio motor. The mix ratio motor adjusts the constituents of the fluid so as to maintain the conductivity of the solution at a selected level. In addition, the system may provide signals to alarm and monitor circuits that are responsive to preselected reading values.

BRIEF DESCRIPTION OF THE DRAWINGS

A better understanding of the invention may be had by reference to the following detailed description, taken in conjunction with the accompanying drawings, in which.

DETAILED DESCRIPTION

Figure 1:
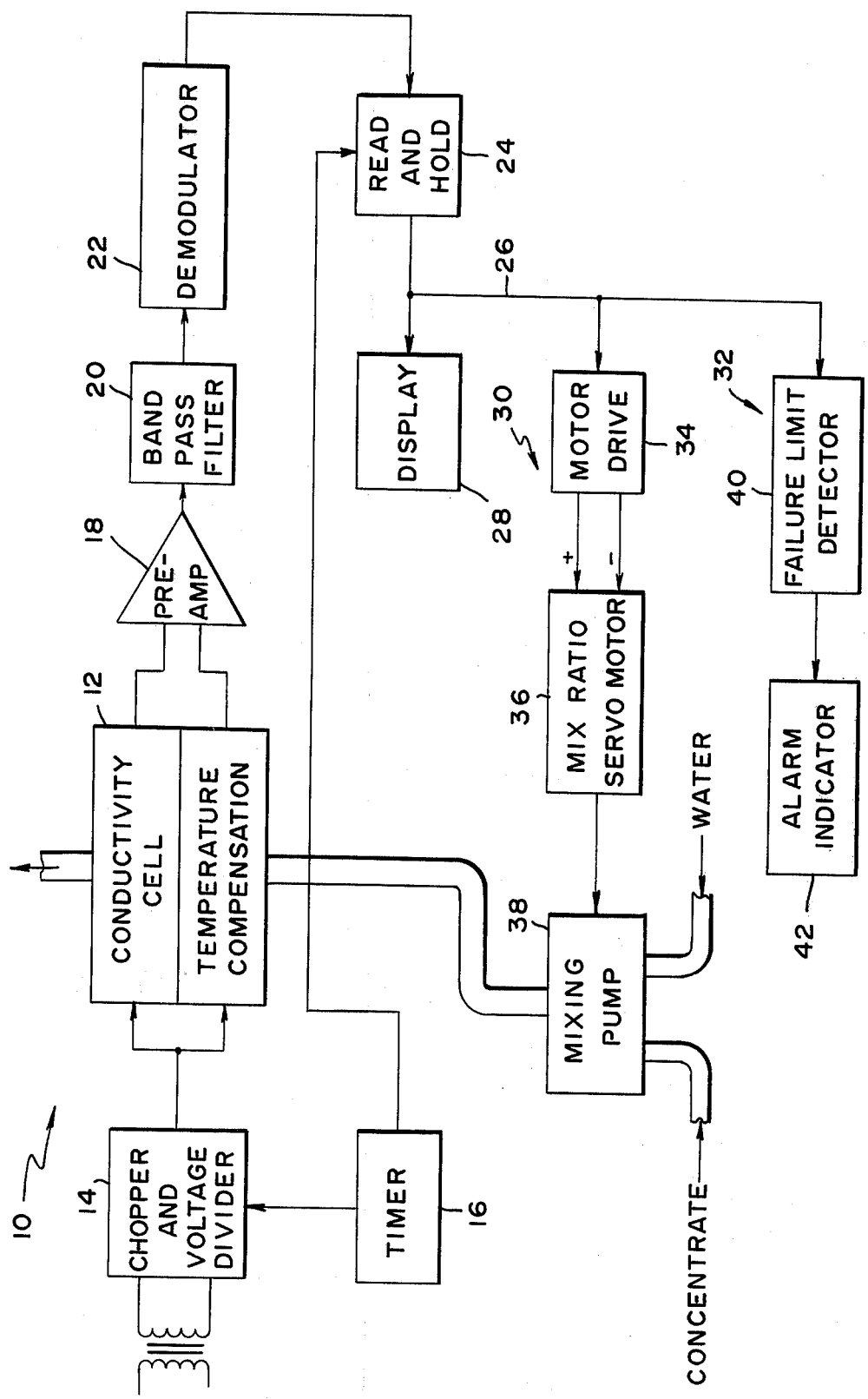
FIG. 1 is a schematic and block diagram representation of a conductivity measurement system in accordance with the invention.

As shown in FIG. 1, a conductivity measurement and control system 10 in accordance with the invention includes a temperature compensated conductivity cell 12, a chopper and voltage divider 14 coupled to drive the conductivity cell 12 with a low voltage, low frequency AC signal, and a timer 16 coupled to impose a duty cycle on the order of 10% or less on the conductivity cell 12. Conductivity cell 112 is connected in a bridge circuit which will be described in more detail hereafter and generates as an output a bridge balance error signal which is indicative of the difference between desired and actual concentration of a salt solution passing through the conductivity cell 12. A preamplifier 18 responds to the output signal from conductivity cell 12 to generate an AC conductivity error signal which has high and low frequency signal components eliminated therefrom by a 60 Hz bandpass filter 20. A demodulator 22 and a read and hold circuit 24 are coupled to receive the output of filter 20 and generate as a continuous output signal a concentration error signal 26 which continuously indicates conductivity error. Circuitry responsive to the DC error signal 26 may include a display 28 which may be a simple panel meter, a mix ratio control circuit 30 and a failure limit detector circuit 32.

The ratio control circuit includes a motor drive circuit 34, a mix ratio servo motor 36, and a mixing pump 38. The mixing pump receives water and a concentrate solution such as a salt solution for a kidney dialysis machine as inputs and, after mixing, emits the two liquids through the conductivity cell 12 in a ratio which is controlled by the mix ratio servo motor 36. The motor drive circuit 34 senses the concentration error signal 26 and processes the error signal to drive the mix ratio servo motor 36 in an advantageous manner which minimizes wear and heat dissipation for mix ratio servo motor 36. Motor drive circuit 34 also drives mix ratio servo motor 36 with a time constant which takes into account the delay between execution of a mix ratio error correction command by mix ratio servo motor 36 and sensing of the resulting mixing ratio concentration by the system 10 to prevent unstable oscillations in mix ratios provided by mixing pump 38.

The failure limit detector circuit 32 includes a failure limit detector 40 and an alarm indicator circuit 42. Failure limit detector 40 senses the conductivity error signal 26 and activates the alarm indicator 42 when the solution concentration error signal 26 moves outside predetermined reference levels. The alarm indicator 42 may operate by illuminating a lamp, by activating an audio signal, or both.

Figure 2:
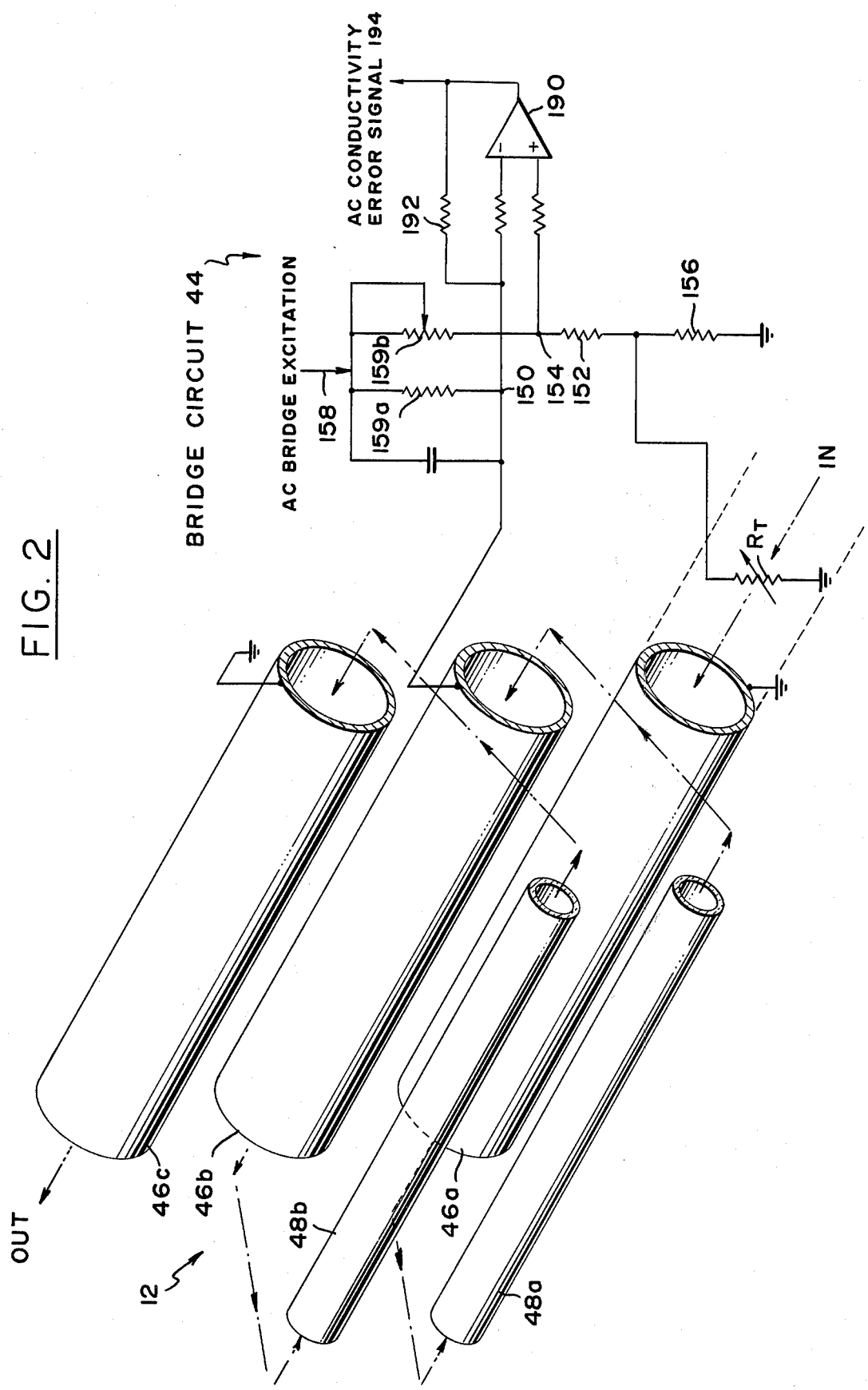
FIG. 2 is a schematic representation of a conductivity cell bridge circuit and preamplifier in accordance with the invention.

As shown in FIG. 2 the conductivity cell is coupled as one leg of a bridge circuit 44 and has three elongated large diameter conductive electrode tubes 46a, 46b and 46c and two elongated small diameter dielectric tubes 48a and 48b. Electrically the fluid paths of the dielectric tubes 48a and 48b are coupled in parallel between one balance point of bridge circuit 44 and ground. However, mixed fluid passes in series pass a thermistor $R_T$ at an inlet to the conductivity cell 12 and then through electrode 46a, tube 48a, electrode 46b, tube 48b and electrode 46c. The five tubes 46, 48 are preferably maintained in parallel spaced relationship.

Figure 3:
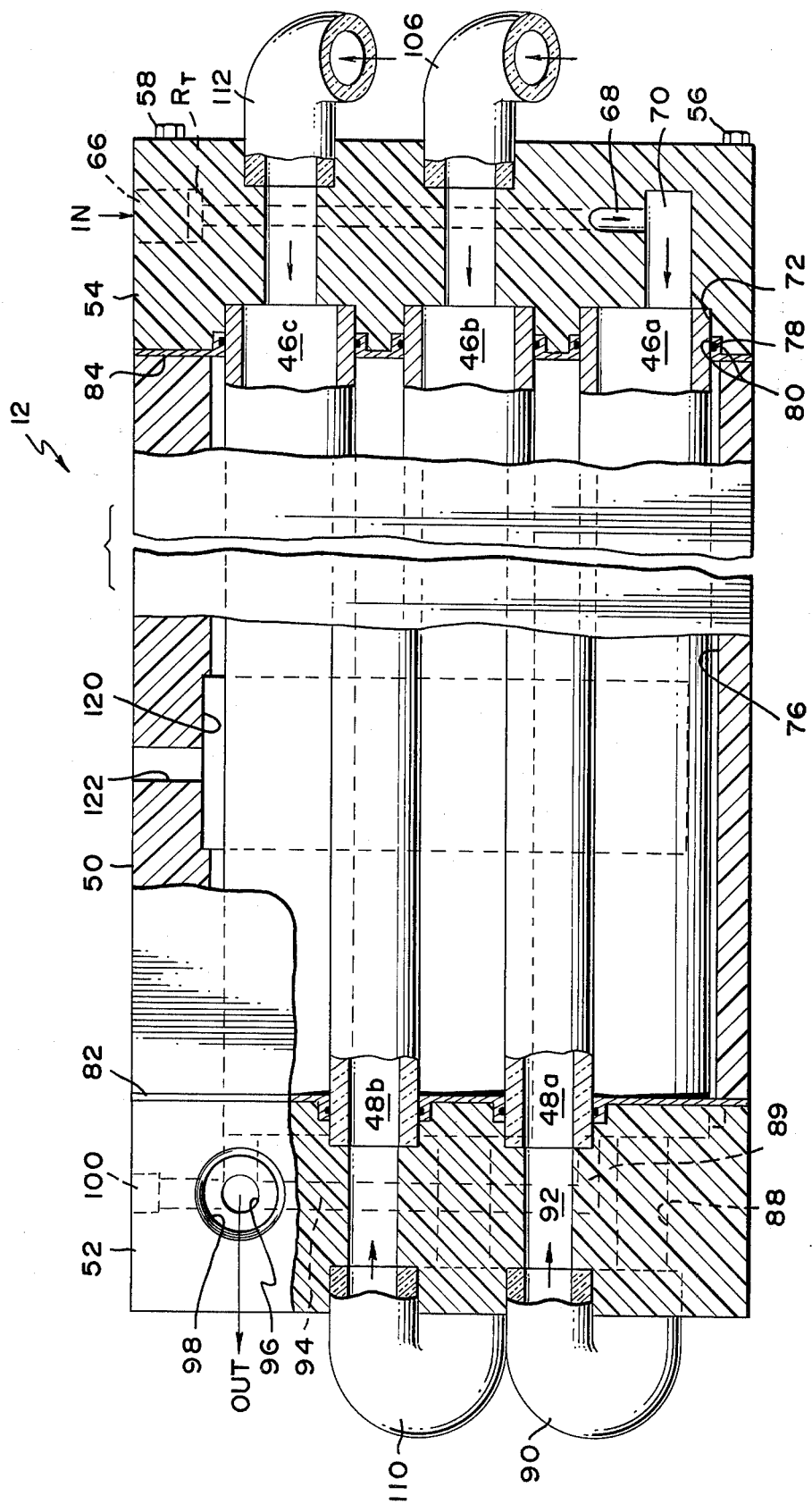
FIG. 3 is a plan view, broken away along two different planes, of the conductivity cell of FIG. 1.
Figure 4:
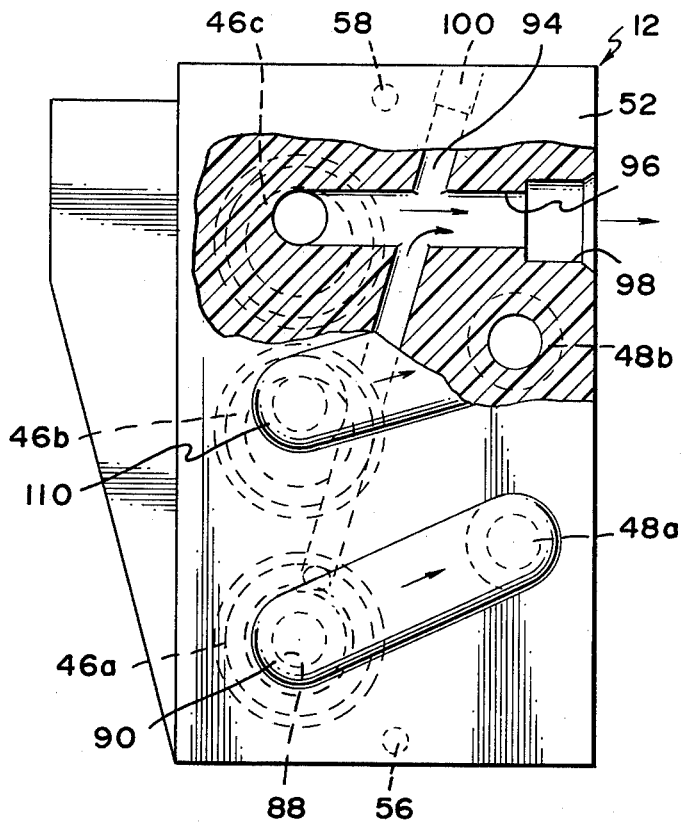
FIG. 4 is a side view, partly broken away, of the conductivity cell of FIG. 2 taken from the left-hand side.
Figure 5:
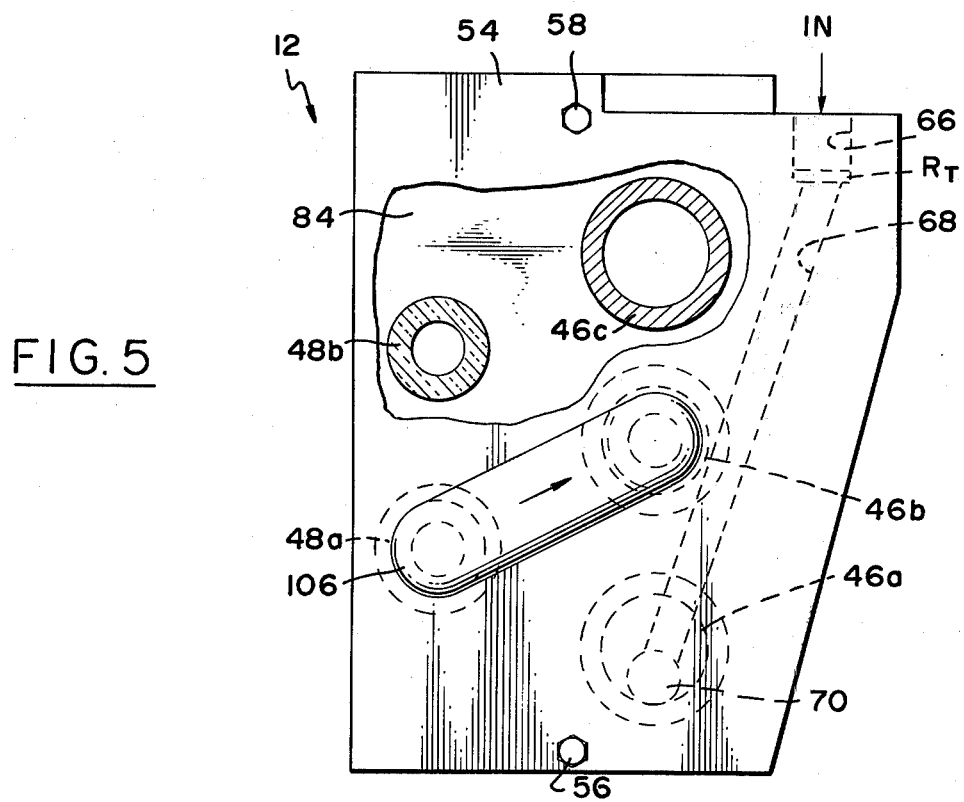
FIG. 5 is a side view, partly broken away, of the conductivity cell of FIG. 2 taken from the right-hand side.

The conductivity cell 12 is further shown in FIGS. 3–5. A left hand portion of FIG. 3 is cut away along a forward plane passing through central axes of the small dielectric tubes 48 and a right hand portion is cut away along a rearward plane passing through central axes of the large diameter electrode tubes 46. The conductivity cell 12 comprises three main structural support elements which includes a central block 50, a left end block 52 and a right end block 54. All may be made of acrylic or PPO plastic or other suitable material with adequate rigidity and resistance to liquids passing through the cell. The center block 50 is not essential but provides good physical support and protection for glass and stainless steel tubes passing horizontally therethrough as well as protection from spilled electrolytes. A pair of bolts 56, 58 extend horizontally through the conductivity cell 12 from the right-hand end block 54 through the central block 50 to threadingly engage the left-hand end block 52 and mechanically support the three blocks in proper juxtaposition.

Mixed solution, the conductivity of which is to be measured, enters the conductivity cell 12 from the mixing pump through an inlet 66 at the rear of the right-hand end block 54 on the top surface thereof. A temperature compensation thermistor $R_T$ is advantageously placed in the fluid path at the opening 66. With the thermistoer $R_T$ so placed the time lag of the thermistor indicating fluid temperature changes substantially matches the time lag required for fluid to enter the cell 12 and begin effecting measured conductivity. The thermistor thus provides an accurate indication of the temperature of the fluid whose conductivity is being measured at any given time.

From the inlet 66 fluids pass downward through a passage 68 in right-hand end block 54 to a horizontally extending bore 70. Bore 70 communicates with a larger horizontally extending bore 72 which receives a right-hand end of an elongated ¾ inch inside diameter by 2½ inch stainless steel cylindrical tube 46a which serves as one of three identical electrodes for the conductivity cell 12. The stainless steel tube 46a is disposed within a lowest bore 76 of five horizontally extending bores through block 50 and is disposed near the rear of the conductivity cell 12. While the manner of sealing the horizontally extending tubes such as tube 74 to the end blocks 52 and 54 is not a critical part of the invention, they may be advantageously sealed by placing O-rings 78 within large diameter bores 80 in the innermost surface of the end blocks with the O-rings 78 being squeezed tightly against the tubes and end blocks and retained by one center block 50. Thin, planar sealing members 82 and 84 with apertures therein for receiving the five tubes may advantageously be placed between the center block 50 and the left-hand end block 52 and right-hand end block 54 respectively. Epoxy or other resin may also be used as a sealing compound in lieu of O-rings 78.

Solution passes from right to left through the horizontally extending stainless steel electrode tube 46a to the left-hand end block 52. A horizontally extending aperture 88 in the left-hand end block 52 carries the solution to a U-shaped glass tube 90 which extends from the left end of left end block 52 and communicates with the left-hand end of the passage 88 to carry fluid to a passage 92 which is forward of, and somewhat above, the passage 88. In addition, a bore 94 extends from the top surface of left-hand end plate 52 downward and toward the rear to communicate with an upper portion of a horizontally extending passage 89 without engaging other horizontally extending passages except for a passage 96 which leads to an outlet 98. Passage 89 is generally parallel to and spaced apart from passage 88. A plug 100 is disposed near the top surface of left-hand end plate 52 to close off tube 94 between outlet leading passage 96 and the top surface. The bore 94 provides a fluid short circuit path between an upper portion of the left-hand end of the lowest horizontal passage and the outlet 98. Approximately half of the fluid flows through passage 94 and bypasses the cell. However, even more importantly, any gas bubbles within the fluid tend to rise and pass through the passage 94. The relatively large cross-sectional area of electrode tube 46a is larger than the cross-sectional areas of the passage 94 and a downstream dielectric tube 48a combined and permits fluid to pass relatively slowly horizontally therethrough to give gas bubbles a chance to rise to the top of the tube 46a. Gravity then causes the bubbles to rise through the bubble trap bypass passage 89 and tube 94.

The presence of a gas bubble within one of the three large diameter stainless steel electrode tubes is not of particular concern, because the lrge cross-sectional area and substantial internal circumference area still permit good electrical coupling of electrode inner surfaces to internal fluids. However, a gas bubble within one of the two smaller 3/16 inch diameter dielectric glass tubes 48 which are coupled between the three electrode tubes 46 would have a substantial effect on measured conductivity. The conductivity of a gas bubble is very low and because the dielectric tubes have a relatively small diameter, a gas bubble may fill a substantial portion of the tube cross-sectional area and cause the fluid path along the tube to appear as a nearly open circuit.

In addition to the bores 89 and 94, which serve as a bubble trap to eliminate most gas bubbles from the solution passing through the small diameter tubes, several precautions are taken to minimize the effects of any bubbles which do escape the bubble trap. First, the two dielectric tubes 48a, 48b are connected in parallel between an electrical input at center electrode tube 46b and a signal ground at upper and lower electrode tubes 46a and 46c. Thus, even if one of the dielectric impedance tubes should become completely blocked by a bubble, the electrical connection of the other glass tube in parallel therewith causes only a 50% change in conductivity to be indicated. In addition, the extremely smooth interior walls of the glass tubes prevent bubbles from sticking to the walls and any bubbles which do enter the tubes are rapidly carried therethrough. It has been found that even carefully bored plastic passages are sufficiently rough that they may decrease the rate at which gas bubbles pass therethrough. Because of their small cross-sectional area in a plane perpendicular to the flow path direction, fluid velocity is fairly high within the glass tubes and bubbles are rapidly carried therethough.

Approximately half of the liquid escapes the bubble trap and passes through the U-shaped glass tube 90 which carries fluid from the lower electrode tube 46a to a lower glass dielectric tube 48a which is disposed somewhat above and forward of tube 46a within the blocks 50, 52 and 54. To minimize field fringing effects and improve the accuracy of electrical measurements, the dielectric tubes 48a and 48b should have a length to diameter ratio of approximately 10:1 or greater. In the present example the glass tubes 48 have an inside diameter of 3/16 inch and a length of 2.5 inches.

The fluid passes horizontally from left to right through glass tube 48a to end block 54 where a U-shaped glass tube 106 provides communication between the tube 48a and horizontally extending stainless steel electrode tube 46b. Electrode tube 46b is disposed near the rear of block 50 approximately midway between the top and bottom. It carries the fluid from right to left where a U-shaped glass tube 110 extends between two positions on the left-hand edge of left end block 52 to carry fluid from center electrode 46b to the upper horizontally extending glass tube 48b. Upper glass tube 48b, which may be substantially identical to lower glass tube 48a is disposed slightly above and forward of center electrode tube 46b and carries the fluid from left to right through block 50. A U-shaped glass tube 112 is disposed adjacent the right-hand edge of right-hand end block 54 to couple fluid from glass tube 48b to upper stainless steel electrode tube 46c. Stainless steel electrode tube 46c carries the fluid from right to left through the block 50 and into communication with outlet passage 96 which carries the fluid in a forward direction through end block 52 near the top thereof to outlet 98.

It should be noted that the spaced disposition of the electrode tubes 46a, 46b and 46c in combination with a low frequency 60 Hz drive excitation minimizes capacitive coupling between electrodes and improves system accuracy. The shape of the electrode tubes 46 is also important. The substantial length and diameter of each electrode tube results in a large internal surface area for good, low impedance surface effect and for good electrical coupling between the fluid within the tube and the tube itself. The substantial length of the electrode tubes permits absorption of stray external currents, i.e., good grounding. In contrast, the dielectric tubes 48 have a length to diameter ratio greater than or equal to 10 and the small inside diameter of these tubes provides a high electrical impedance fluid path and negligible surface effect.

An aperture 120 in the forward face of block 50 extends into communication with all three stainless steel electrode tubes 46a, 46b and 46c. The aperture 120 may be utilized for coupling electrical conductors to these electrode tubes and the conductors may then be passed through a bore 122 which extends between the aperture 120 and the top of block 50. After making electrical connection, the aperture 120 may be filled with epoxy resin or other suitable material to mechanically protect the tubes and seal them against any material which might enter the aperture and effect the apparent conductivity of the fluid passages.

The electrical control portion of the mixing ratio control system is shown in FIGS. 1, 2, 6 and 7. The conductivity cell 12 is coupled with the lower glass tube 48a providing a concentration dependent resistance between central electrode tube 46b and lower electrode tube 46a. Similarly, upper glass tube 48b provides a concentration dependent resistance between central electrode tube 46b and upper electrode tube 46c. The upper and lower electrode tubes 46a, 46c are coupled together and to the ground of the electronic control circuitry. The central electrode tube 46c is coupled to a first bridge center balance point 150. The thermistor $R_T$ is coupled to ground on one terminal thereof and through a 715 ohm resistor 152 to a second bridge terminal center balance point 154 and also through a 2.67 K resistor 156 to ground. Resistors 152 and 156 match temperature dependent conductivity variations in the two lower legs of the bridge so that temperature changes in the fluid passing through the conductivity cell 12 cause like voltage changes at bridge midpoints 150 and 154. The bridge is driven with a 60 Hz one volt peak-to-peak AC signal 158 which is coupled through a 4.75 K resistor 159a to midpoint 150 and through a 2.74 K resistor 159b to midpoint 154. A 0.0068 $\mu f$ capacitor shunts resistor 159a.

The one volt peak-to-peak bridge excitation signal 158 is derived from a 6 volt AC signal 160 provided by a step down utility line voltage transformer 162. The 6 volt AC signal 160 is reduced in a voltage divider circuit comprising a 6.81 K resistor 164 and 475 ohm resistor 180 which are coupled in series between signal 160 and ground. A field effect transistor 166 which may be a 2N5458 is coupled to operate in a switching mode and selectively couples the input of the bridge circuit to the common point of resistors 164 and 180 to generate signal 158. System timing is provided by an NE555V integrated timing circuit which controls the energization of the conductivity sensing bridge circuit to provide a duty cycle of approximately 9%. The timer 170 is arranged to cycle on for 0.5 seconds and then turn-off for 5 seconds. One output of timer 170 is coupled through a 22.1 K resistor to the base of an NPN transistor 172 having the emitter thereof coupled to −15 volts. During approximately 9% of each timing cycle, the base of transistor 172 is driven low to cause the transistor to turn off and allow the collector voltage to increase toward +15 volts which is provided through a 33.2 K resistor 174. The high collector voltage reverse biases a pair of diodes 176 and 178. Reverse biasing of diode 176 permits the gate voltage of transistor 166 to be coupled through a 100K resistor 181 to the drain thereof to permit transistor 166 to turn on and drive signal 158 with the one volt peak-to-peak 60 Hz AC signal appearing between resistors 164 and 180.

Reverse biasing of diode 178 enables one input to a second FET transistor 184. A second input is controlled by a diode 186 and a differential amplifier 188. During negative half cycles of the 60 Hz AC signal the output of amplifier 188 goes high to back bias diode 186 and fully enable transistor 184. During positive half cycles of the 60 Hz AC signal the output of amplifier 188 is driven low and is coupled through diode 186 to the gate FET transistor 184 to turn it off. Thus, FET transistor 184 serves as a half wave rectifier and phase detector to pass bridge output signals only during the 9% of a duty cycle that the bridge is activated and only during the negative half cycles of said bridge activation. At the end of an approximately 0.5 second "on" period the output of timer 170 goes high to turn on transistor 172 and drive the collector thereof toward −15 volts. This forward biases diodes 176 and 178 to disable transistors 166 and 184 respectively.

A differential preamplifier 190 has negative and positive inputs coupled through 10K resistors to bridge center points 150 and 154 respectively. The output of amplifier 190 is coupled through a 22.1 K resistor 192 to drive the midpoint 150 with a current which will keep the voltage at midpoint 150 equal to the voltage at point 154. As explained above, FET transistor 184 acts as a phase detector to permit the ratio control circuit to respond only during negative half cycles of the 60 Hz AC excitation voltage. Therefore, the following description will be in terms of what happens during the negative half cycle and will ignore the positive half cycle.

If the concentration of the salts in the mixed solution increases, the conductivity thereof will also increase and the bridge midpoint 150 will become less negative, or positive, relative to midpoint 154. The output of amplifier 150 will then be driven negative until sufficient current is drawn through resistor 192 to decrease the voltage at bridge midpoint 150 and balance the bridge. The voltage at the output of amplifier 190 will be −22,100 times the current required to balance the bridge and will be AC in nature. The output of amplifier 190 thus generates an AC conductivity error signal 194 which becomes increasingly negative as the solution salt concentration increases beyond a predetermined reference concentration.

The AC error signal 194 is passed through a 60 Hz bandpass filter amplifier 196 which includes a series 0.22 microfarad capacitor 198 and a non-inverting operational amplifier 200. The output 202 of bandpass filter amplifier 196 is coupled through a low pass output filter having a 4.75 K resistor 204 coupled between circuit output 202 and the output of amplifier 200 and a parallel combination of a 10K resistor 206 and a 470 picofarad capacitor 208 coupled between circuit output 202 and ground. Bandpass filter amplifier 196 provides a maximum signal amplitude at 60 Hz. This 60 Hz error signal 202 is coupled through the source and drain terminals of transistor 184 to a read and hold circuit 210. The read out hold circuit 210 comprises a 0.47 microfarad capacitor 212 which is connected to ground between an 806 K input resistor 214 and a 100 K output resistor 216. This RC combination provides the input of the read and hold circuit 210 with a time constant of about 0.4 seconds, which is quite long with respect to the period of the excitation signals. With the solution concentration increasing, a negative signal will be imparted to the read and hold circuit 210.

A non-inverting amplifier 220 is coupled to the output of read and hold circuit 210 and provides a 2:1 voltage amplification. The output of amplifier 220 generates the concentration error signal 26 as shown in FIG. 1. The input resistance of amplifier 220 is approximately $10^{12}$ ohms to minimize discharge of holding capacitor 212.

The motor drive amplifier 34 responds to concentration error signal 26 and has a non-inverting gain of 5.75:1. The output of servo motor drive amplifier is coupled through oppositely poled diodes 222 and 224 to positive and negative motor drive inputs respectively. The diodes 222 and 224 provide a motor control dead band for increased stability. The long time constant of the sample and hold circuit 210 reduces the bandwidth of the motor control feedback circuit to allow for transport lag in the lines and mixing chamber leading to the conductivity cell and thereby prevent hunting or oscillation of the servo control loop.

The concentration error signal 26 is also coupled to the display 28 and failure limit detector circuit 32 having a portion thereof designated alarm circuit 44. The display 28 may be implemented as a milliameter coupled between the midpoint of a voltage divider circuit and ground. The voltage divider circuit may be coupled to bias the meter toward a desired concentration reading when the concentration error signal 26 is at zero potential.

Figure 7:
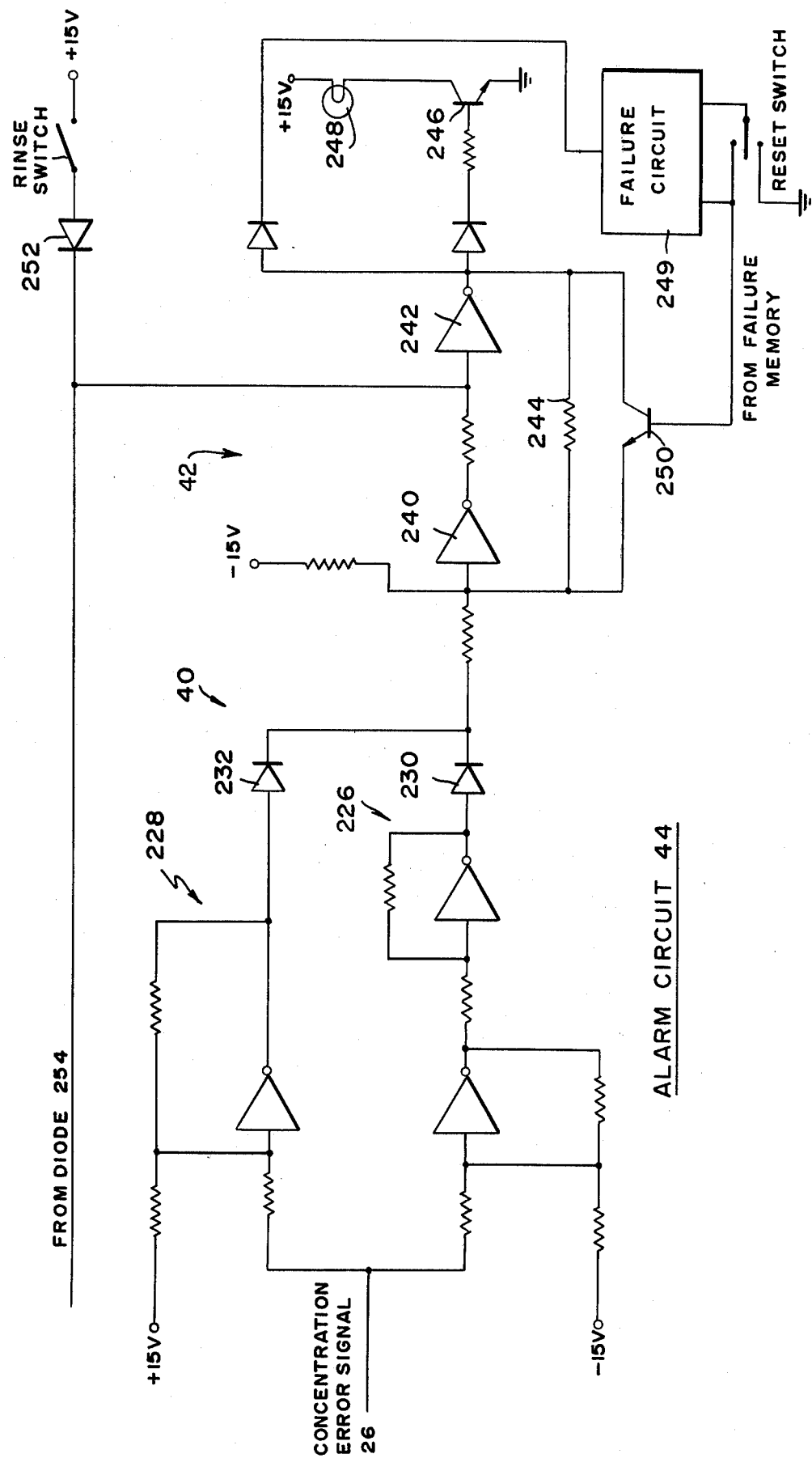
FIG. 7 is a schematic representation of an alarm circuit shown in FIG. 6.

As shown in FIG. 7, the failure limit detector 40 may advantageously comprise a pair of plus and minus threshold detectors 226, 228 respectively which are ORed through a pair of diodes 230, 232 respectively. Any time the concentration error 26 exceeds one of the predetermined threshold safety limits, the output of failure limit detector limit 40 is driven high to in turn drive high the normally low input of an inverter 240 within the alarm indicator circuit 42. Inverter 242 is coupled to the output of inverter 240 and an 806 K resistor 244 provides positive feedback between the output of inverter 242 and the input of inverter 240 to provide a certain amount of hysteresis to the alarm indicator circuit 42 to prevent removal of the alarm indication signal until the concentration error signal 26 is well within the predetermined safety limits. The output of inverter 242 is coupled to drive the base of an NPN lamp driver transistor 246 so that whenever the output of inverter 242 goes high a lamp 248 is illuminated.

Figure 6:
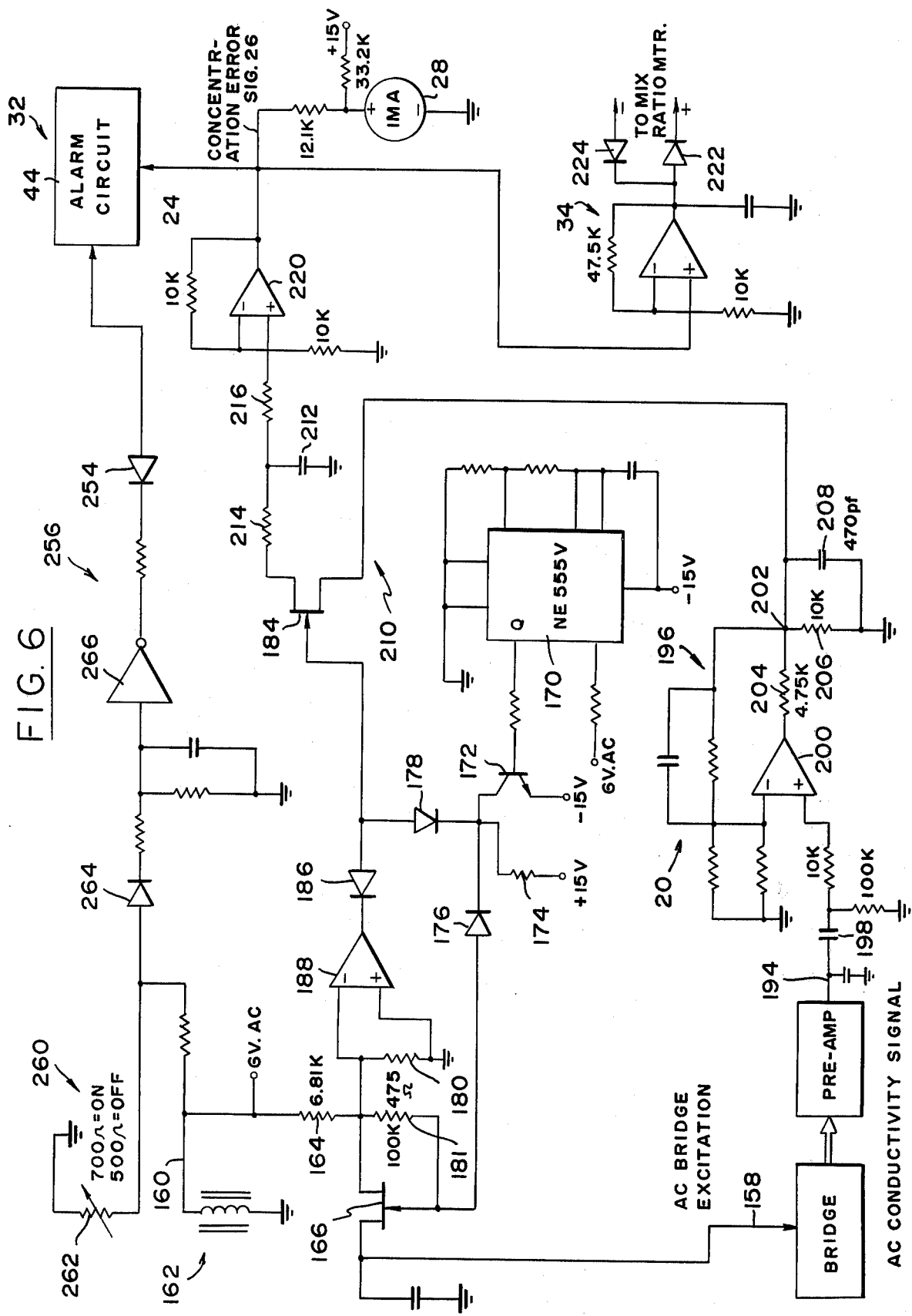
FIG. 6 is a schematic diagram of processing circuits depicted in the block diagram of FIG. 1.

The output of inverter 242 may also be coupled to a failure circuit 249 which may terminate power to mixing pump 38 and latch the failure condition in a memory. The latched memory may in turn generate a signal to turn on a transistor 250 is a positive feedback path between the output of inverter 242 and the input of inverter 240 to latch the error condition until the failure memory is manually reset. In order to allow operation of the mixing pump 38 during a system rinsing cycle, a rinse switch may be coupled to provide a high voltage through a diode 252 and latch the input to inverter 242 in a high voltage no alarm indication condition. The input to inverter 242 is also ORed through a diode 254 to a concentrate monitor circuit 256 as shown in FIG. 6.

A concentrate monitor sensor 260 is coupled to sense the presence of concentrate solution in a hydraulic passage 262. The electrical resistance of hydraulic passage 262 is coupled in a voltage divider circuit between the 6 volt excitation signal and ground. With the resistance of passage 262 increased, due to the absence of concentrate solution, the divided voltage goes sufficiently high during positive half cycles of the excitation voltage to forward bias a diode 264 and drive the input of an inverter 266 positive to cause the output thereof to go low. The low output is then coupled through diode 254 to drive the input to inverter 242 and provide an alarm indication. This arrangement permits the out of concentrate condition to be detected before the concentrate runs out and the mixing pump 38 begins pumping pure water.

While there has been shown and described above a concentration control system for the purpose of enabling a person of ordinary skill in the art to make and use the invention, it will be appreciated that the invention is not limited thereto. Accordingly, any modifications, variations or equivalent arrangements within the scope of the attached claims should be considered to be within the scope of the invention.

That which is claimed is:

1. A system for measuring the conductivity of a solution comprising:
    a fluid conduit system comprising first, second and third elongated, conductive, tubular electrode chambers each having a diameter providing at least a minimum cross-sectional area and a length greater than the diameter, first and second nonconductive tubular chambers serially connected between the first and second, and second and third electrode chambers respectively to provide a continuous fluid path between the first and third electrode chambers, the first and second chambers each having a diameter providing a cross-sectional area less than the minimum cross-sectional area, and a length greater than 10 times the diameter; and
    circuit means coupled to said conductive electrode chambers for measuring conductance of a fluid within the fluid conduit system.

2. The invention as set forth in claim 1 above, wherein said electrode chambers comprise a set of three spaced-apart chambers, wherein the conductive surfaces of first and third chambers are grounded, and wherein the circuit means is coupled to a second chamber for measuring conductance changes.

3. The invention as set forth in claim 2 above, wherein said fluid conduit system comprises substantially cylindrical electrode chambers disposed in substantially, horizontal parallel and spaced-apart relation, and wherein said non-conducting passageways are cylindrical glass walled conduits disposed substantially parallel to said electrode chambers and spaced apart therefrom, and wherein said system further includes conduits coupling different terminal portions of said electrode chambers and passageways such that a continuous path for the solution is provided.

4. The invention as set forth in claim 2 above, wherein said circuit means comprises a bridge network, one arm of which comprises the conductance of a solution within said conduit system, said bridge network further including means for indicating variations in the conductance of the solution within the conduit system.

5. The invention as set forth in claim 4 above, wherein said circuit means further includes thermistor means disposed in heat responsive relation to the solution within said conduit system proximate an inlet thereof, and in an arm of said bridge network, said thermistor means having a temperature characteristic varying in compensatory fashion for variations in the conductivity of said solution in accordance with temperature.

6. The invention as set forth in claim 3 above, wherein the total interior fluid engaging area of said electrode chambers is substantially greater than the cross-sectional area thereof.

7. The invention as set forth in claim 1 above, wherein said circuit means includes means for sensing conductance changes periodically during sensing intervals, and means for storing values indicating the sensed changes between sensing intervals.

8. The invention as set forth in claim 7 above, wherein said circuit means includes means providing alternating current excitation of the fluid conduit system only during the sensing intervals and means providing measurement during a sensing interval of conductance changes, and wherein each said sensing interval is approximately 10% or less of the interval between sensing intervals.

9. A system for measuring the conductivity of a solution comprising:
    a fluid conduit system comprising a set of at least three spaced-apart electrode chambers having interior conductive surfaces, and interconnecting non-conducting passageways between said electrode chambers, said passageways having a smaller cross-sectional area than said chambers and lengths substantially greater than their diameters; and
    circuit means coupled to said electrode chamber conductive surfaces for measuring conductance changes in the solution within said conduit system, the current means including means for sensing conductance changes periodically during sensing intervals using low voltage alternating current and means for storing values indicating the sensed changes between sensing intervals, said sensing intervals having a duration of 10% or less of the time between intervals, the circuit means further including preamplifier means responsive to said low voltage signal, bandpass filter means responsive to the frequency of said alternating current signal, synchronous demodulator means responsive to the signal from said bandpass filter means and operating at said alternating current frequency; and sample and hold means responsive to the signal from said synchronous demodulator.

10. The invention as set forth in claim 9 above, wherein said circuit means further includes timing control means coupled to said bridge network means and said synchronous demodulator means.

11. A conductive cell having a liquid conduit system coupled to provide a flow path for a liquid, the conductivity of which is to be measured, from a cell inlet to a cell outlet, the liquid conduit system comprising:
    an elongated first electrode having an aperture therein with a cross-sectional area in a plane perpendicular to the direction of fluid flow, an inlet end and an outlet end, the inlet end being coupled to receive fluid from the cell inlet;
    a first dielectric element having an elongated aperture extending therethrough between an inlet end and an outlet end, the inlet end being coupled to receive liquid from the outlet end of the first electrode below the top thereof and the aperture having a cross-sectional area in a plane perpendicular to the direction of liquid flow therethrough which is less than the cross-sectional area of the first electrode;
    an elongated second electrode having an aperture therein coupled to carry liquid between the outlet end of the dielectric element aperture and the cell outlet, the cell providing a fluid path between the first and second electrodes for a conductive liquid flowing therebetween with at least a portion of an electrical path between the first and second electrodes being formed solely by a fluid flowing along the fluid path, and a second dielectric element having an elongated aperture extending therethrough between an inlet end coupled to a vertically upwardmost portion of the aperture in the first electrode at the outlet end thereof and an outlet end that is disposed vertically above the inlet end of the aperture in the second dielectric element, the outlet of the aperture in the second dielectric element being coupled to provide a fluid path that is in parallel with the aperture through the first dielectric element, the aperture in the second dielectric element having a cross-sectional area, and the sum of the cross-sectional areas of the first and second dielectric elements being less than the corss-sectional area of the first electrode.

12. A conductive cell having a liquid conduit system coupled to provide a flow path for a liquid, the conductivity of which is to be measured, from a cell inlet to a cell outlet, the liquid conduit system comprising:

an elongated first electrode having an aperture therein with a cross-sectional area in a plane perpendicular to the direction of fluid flow, an inlet end and an outlet end, the inlet end being coupled to receive fluid from the cell inlet;

a dielectric element having an elongated aperture extending therethrough between an inlet end and an outlet end, the inlet end being coupled to receive liquid from the outlet end of the first electrode and the aperture having a cross-sectional area in a plane perpendicular to the direction of liquid flow therethrough which is less than the cross-sectional area of the first electrode;

an elongated second electrode having an aperture therein coupled to carry liquid between the outlet end of the dielectric element aperture and the cell outlet, the cell providing a fluid path between the first and second electrodes for a conductive liquid flowing therebetween with at least a portion of an electrical path between the first and second electrodes being formed solely by a fluid flowing along the fluid path; and a bubble trap coupled to remove gas bubbles from the liquid flow path before the bubbles reach the inlet end of the aperture extending through the dielectric element.

13. The conductivity cell according to claim 12 above, wherein the bubble trap comprises a tubular path extending between the cell outlet and a connection point at an upper portion of the liquid flow path which is upstream from the inlet to the dielectric element aperture, the cell outlet being disposed above the connection point and the cross-sectional area of the tubular path in a plane perpendicular to the liquid flow direction being less than the difference between the cross-sectional areas of the apertures through the first electrode and the dielectric element, the directions upper and above being relative to gravitational type forces acting upon a liquid passing through the cell.

14. The conductivity cell according to claim 13 above, wherein the aperture through the dielectric element is defined by very smooth interior wall surface.

15. The conductivity cell according to claim 14 above, wherein said interior wall surface is glass.

16. The conductivity cell according to claim 13 above, comprising a third electrode positioned along the liquid flow path and a second dielectric element with an elongated aperture extending therethrough between the second and third electrodes, the electrical paths through liquid passing through the first mentioned and second dielectric elements being electrically coupled in parallel.

17. A physically compact and electrically efficient conductivity cell comprising three large diameter conductive tubes disposed to extend in co-extensive, parallel, closely spaced relationship between first and second end blocks at opposite ends thereof, two dielectric tubes of diameter less than the diameters of the conductive tubes disposed to extend parallel to and co-extensive with the conductive tubes in close proximity thereto between first and second end blocks at opposite ends thereof, first and second end blocks coupled to sealingly engage opposite ends of the three conductive and two dielectric tubes and means associated with the first and second end blocks for coupling the ends of the conductive and dielectric tubes to form an alternately conductive and dielectric continuous serial flow path through all of the tubes.

18. A conductivity cell comprising three large diameter conductive tubes disposed to extend in parallel, spaced apart relationship beween first and second end blocks at opposite ends thereof, two dielectric tubes of diameter less than the diameters of the conductive tubes disposed to extend parallel to the conductive tubes between first and second end blocks at opposite ends thereof, first and second end blocks coupled to sealingly engage opposite ends of the three conductive and two dielectric tubes and means associated with the first and second end blocks for coupling the ends of the conductive and dielectric tubes to form an alternately conductive and dielectric continuous serial flow path through all of the tubes, and a bubble trap coupled to remove bubbles from the flow path before they reach a first dielectric tube along the flow path.

* * * * *

UNITED STATES PATENT AND TRADEMARK OFFICE
CERTIFICATE OF CORRECTION

PATENT NO. : 4,035,719
DATED : July 12, 1977
INVENTOR(S) : Robert L. Anderson

It is certified that error appears in the above-identified patent and that said Letters Patent are hereby corrected as shown below:

Column 1, line 41, "impendence" should read --impedance--. Column 2, line 37, after "cell" (second occurrence) and before "is", "112" should read --12--. Column 3, line 13, after "Fig. 2" and before "the" insert a comma (--,--); line 51, "thermistoer" should read --thermistor--. Column 4, line 48, before "cross-sectional", "lrge" should read --large--. Column 6, line 39, after "and" and before "475 ohm", insert --a--. Column 9, line 44, after "horizontal" and before "parallel", insert a comma (--,--).

Signed and Sealed this

Fourth Day of October 1977

[SEAL]

Attest:

RUTH C. MASON
Attesting Officer

LUTRELLE F. PARKER
Acting Commissioner of Patents and Trademarks